United States Patent
Shibuya et al.

(10) Patent No.: US 10,551,299 B2
(45) Date of Patent: Feb. 4, 2020

(54) MULTIPASS CELL, GAS ANALYZER, AND METHOD FOR MANUFACTURING MIRROR FOR MULTIPASS CELL

(71) Applicant: HORIBA, Ltd., Kyoto (JP)

(72) Inventors: Kyoji Shibuya, Kyoto (JP); Masahiro Nakane, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 16/150,877

(22) Filed: Oct. 3, 2018

(65) Prior Publication Data
US 2019/0101487 A1 Apr. 4, 2019

(30) Foreign Application Priority Data
Oct. 3, 2017 (JP) .................................. 2017-193889

(51) Int. Cl.
*G01N 21/03* (2006.01)
*G01N 21/47* (2006.01)
*G01N 21/05* (2006.01)

(52) U.S. Cl.
CPC ......... *G01N 21/031* (2013.01); *G01N 21/474* (2013.01); *G01N 2021/058* (2013.01); *G01N 2021/4761* (2013.01); *G01N 2201/068* (2013.01)

(58) Field of Classification Search
CPC ............... G01N 21/031; G01N 21/474; G01N 2021/058; G01N 2021/4761; G01N 2201/068
See application file for complete search history.

(56) References Cited

U.S. PATENT DOCUMENTS

| 6,563,583 B2 | 5/2003 | Ortyn et al. |
| 2008/0212217 A1 | 9/2008 | Robert |
| 2010/0267010 A1 | 10/2010 | Goebel et al. |
| 2012/0242989 A1* | 9/2012 | So .................... G02B 5/10 356/402 |
| 2017/0102315 A1 | 4/2017 | Sawyers |

FOREIGN PATENT DOCUMENTS

JP 2010-243270 A 10/2010

OTHER PUBLICATIONS

Hao Lu-Yuan et al., Cylidrical Mirror Multipass Lissajous System for Laser Photoacoustic Spectroscopy, Review of Scientific Instruments, AIP, Melville, NY, US, May 1, 2002, vol. 73, No. 5, pp. 2079-2085.
EESR dated Dec. 20, 2018 issued for European patent application No. 18 197 909.7, 12 pgs.

* cited by examiner

*Primary Examiner* — Jamil Ahmed
(74) *Attorney, Agent, or Firm* — Brooks Kushman P.C.

(57) ABSTRACT

To provide a multipass cell permitting a reduction in a volume of an inner space into which sample gas is introduced, there are provided: a cell main body with the inner space into which the sample gas is introduced; and a pair of mirrors provided oppositely to each other in the inner space, wherein light incident from an incidence window of the cell main body is subjected to multireflection between the pair of mirrors and is emitted from an emission window of the cell main body, wherein: each of the mirrors is shaped such that light spots formed on a reflecting surface of each of the mirrors are scattered in an elongated region of a predetermined width through the light multireflection; and each of the mirrors is formed into an elongated shape along a longitudinal direction of the elongated region.

12 Claims, 13 Drawing Sheets

MULTIPASS CELL, GAS ANALYZER, AND METHOD FOR MANUFACTURING MIRROR FOR MULTIPASS CELL

CROSS-REFERENCE TO RELATED APPLICATION

This application claims priority to Japanese Application No. 2017-193889, filed Oct. 3, 2017, the disclosure of which is incorporated in its entirety by reference herein.

TECHNICAL FIELD

The present invention relates to a multipass cell, a gas analyzer including the multipass cell, and a method for manufacturing a mirror for the multipass cell.

BACKGROUND ART

Some gas analyzers using light absorption as disclosed in Patent Literature 1 use what is called a multipass cell which has a pair of mirrors arranged oppositely to each other in a cell main body, into which sample gas is introduced, to cause multireflection of light between the mirrors.

The use of the multipass cell as described above increases a light path length, thus permitting an increase in a distance of interaction between the light and the sample gas and permitting an improvement in sensitivity.

However, the multipass cell disclosed in Patent Literature 1 is of a type called a Herriot cell, which uses, as the pair of mirrors, spherical mirrors with reflecting surfaces of a circular shape in a plan view, so that a height and a width of the cell main body needs to be larger than those of the spherical mirrors, and there is limitation on a reduction in a volume of an inner space of the cell main body.

Consequently, there is also limitation on an improvement in a replacement speed of the sample gas introduced into the inner space, raising a problem of failure in obtaining a response speed required for analysis, for example, upon measurement of exhaust gas or the like whose discharge amount of each component fluctuates in accordance with a behavior of an internal combustion engine.

CITATION LIST

Patent Literature

Patent Literature 1: Japanese Unexamined Patent Application Publication No. 2010-243270

SUMMARY OF INVENTION

Technical Problem

Thus, the present invention has been made to solve the problem described above, and it is a main object of the present invention to provide a multipass cell permitting a reduction in a volume of an inner space into which sample gas in introduced.

Solution to Problem

Specifically, a multipass cell according to one aspect of the present invention includes: a cell main body with an inner space into which sample gas is introduced; and a pair of mirrors including a first mirror and a second mirror provided oppositely to each other in the inner space, wherein light incident from an incidence window of the cell main body is subjected to multireflection between the pair of mirrors and is emitted from an emission window of the cell main body, wherein: the pair of mirrors are configured such that light spots formed on a reflecting surface of each of the mirrors are scattered in an elongated region of a predetermined width through the light multireflection; and each of the mirrors is formed into an elongated shape along a longitudinal direction of the elongated region.

With the multipass cell configured as described above, the pair of mirrors are configured such that the light spots formed on the reflecting surface are scattered in the elongated region of the predetermined width and are formed into elongated shapes along the longitudinal direction of the elongated region, thus permitting more drastic downsizing of the pair of mirrors than that in a conventional case.

Consequently, a required volume of the inner space of the cell main body can be made very small, consequently making it possible to improve a replacement speed of the sample gas introduced into the inner space, which permits a dramatic improvement in a response speed of analysis.

To achieve the downsizing of the mirrors while increasing a light path length through the multireflection, a length of each of the mirrors along the longitudinal direction of the elongated region is preferably twice or more and more preferably three times or more as long as a length of each of the mirrors along a width direction orthogonal to the longitudinal direction.

As the multipass cell, there is a type called an astigmatic Heriot cell which is different from the Heriot cell described in Background Art. This type uses, as the pair of mirrors, toroidal mirrors having mutually orthogonal two axes with different curvature radiuses instead of using the spherical mirrors, and by focusing the light spots on a region where the reflecting surface is located, use efficiency of the mirrors is improved, consequently achieving the downsizing of the mirrors.

However, to fabricate the toroidal mirrors with high accuracy, an advanced processing technology is required, resulting in a more remarkable increase in manufacturing costs of the toroidal mirrors as compared to those of the spherical mirrors.

Thus, to achieve downsizing of the volume of the inner space without leading to the remarkable increase in the manufacturing costs, it is preferable that each of the mirrors be configured such that the light spots are scattered in the elongated region by use of the spherical mirror.

Examples listed as embodiments for scattering the light spots on the elongated region of the predetermined width include an embodiment such that the light spots are scattered on a straight line, a parabola, or an ellipse in the elongated region.

When a length of the cell main body along a longitudinal direction of the mirror is longer than a length of the cell main body along a width direction of the mirror, the cell main body is of a flat shape, which can provide a smaller volume of the inner space than that of a conventional cell main body.

To use the multipass cell, positions of the mirrors need to be adjusted such that light incident from an incidence window of the cell main body is subjected to multireflection between the pair of mirrors and is emitted from an emission window of the cell main body. Examples listed as methods for adjusting the aforementioned positions include a method for pushing and pulling a plurality of sections of the mirror by using a plurality of adjustment screws to thereby adjust orientation of the mirrors while varying a lifting direction and a heading direction of the mirrors.

However, the method for the adjustment described above adjusts the orientation of the mirrors by repeating operation of pushing and pulling the plurality of adjustment screws, thus requiring great labor for the adjustment and also resulting in an increase in the number of components as a result of providing the plurality of adjustment screws, which leads to a cost increase accordingly.

Thus, it is preferable that the cell main body have at least two cell elements forming the cell main body, that the first mirror be fixed at one of the at least two cell elements and the second mirror be fixed at another one of the at least two cell elements, and that a slide mechanism of sliding, with respect to the one of the cell elements, the another one of the cell elements be provided between the at least two cell elements.

With the multipass cell configured as described above, the mirrors are respectively fixed at the at least two cell elements forming the cell main body and the slide mechanism of sliding, with respect to the one of the cell elements, the another one of the cell elements is provided between these cell elements, and thus the position adjustment of the mirrors can be performed by sliding the another one of the cell elements by the slide mechanism.

Consequently, it is possible to simply adjust the positions of the mirrors with a small number of components without using, for example, the adjustment screws for varying the lifting direction and the heading direction of the mirrors.

To more simplify the positioning of the mirrors, it is preferable that each of the mirrors be positioned in a direction orthogonal to a predetermined reference plane with respect to the reference plane, and that the slide mechanism slide, with respect to the one of the cell elements, the another one of the cell elements along an in-plane direction parallel to the reference plane.

With such configuration, the position adjustment of the mirrors in the direction orthogonal to the reference plane can no longer be required, making it possible to complete the position adjustment of the mirrors by sliding the cell element along the in-plane direction parallel to the reference plane.

To configure the slide mechanism with a small number of components without placing another member between the at least two cell elements, it is preferable that the slide mechanism have: a first slide surface formed at the one of the cell elements; and a second slide surface formed at the another one of the cell elements and making surface contact with the first slide surface, and change positions of the pair of mirrors in the in-plane direction.

It is preferable that the slide mechanism has a guide surface making contact with the another one of the cell elements and regulating a slide direction of the another one of the cell elements.

With such configuration, it is possible to complete the position adjustment of the mirrors by sliding the cell element in a slide direction regulated by the guide surface, resulting in more simplified positioning of the mirrors.

Moreover, a gas analyzer according to another aspect of the present invention includes: the multipass cell described above; a light source emitting light to the incidence window; a light detector detecting the light emitted from the emission window; and an information processor analyzing the sample gas based on a light intensity signal detected by the light detector.

With such a gas analyzer, the same effects as those of the multipass cell described above can be provided.

Further, a method for manufacturing a mirror for a multipass cell according to still another aspect of the present invention refers to a method for manufacturing a pair of mirrors including a first mirror and a second mirror being provided oppositely to each other in an inner space of a cell main body into which sample gas is introduced and configuring a multipass cell with the cell main body, wherein a pair of prototype mirrors including a first prototype mirror and a second prototype mirror serving as prototypes of the pair of mirrors are cut into elongated shapes, and the shapes of the pair of prototype mirrors are changed such that light spots formed on reflecting surfaces of the pair of mirrors are scattered in an elongated region of a predetermined width through light multireflection.

With the mirror of an elongated shape manufactured by such a method, more drastic downsizing than that in a conventional case can be achieved. Consequently, a required volume of the inner space of the cell main body can be made very small, consequently making it possible to improve a replacement speed of the sample gas introduced into the inner space and permitting a dramatic improvement in a response speed of analysis.

Advantageous Effects of Invention

According to the present invention configured as described above, the volume of the inner space into which the sample gas is introduced can be made small, making it possible to improve the replacement speed of the sample gas and permitting the improvement in the response speed of the analysis.

DESCRIPTION OF EMBODIMENTS

Hereinafter, one embodiment of a gas analyzer according to the present invention will be described with reference to the drawings.

Figure 1:
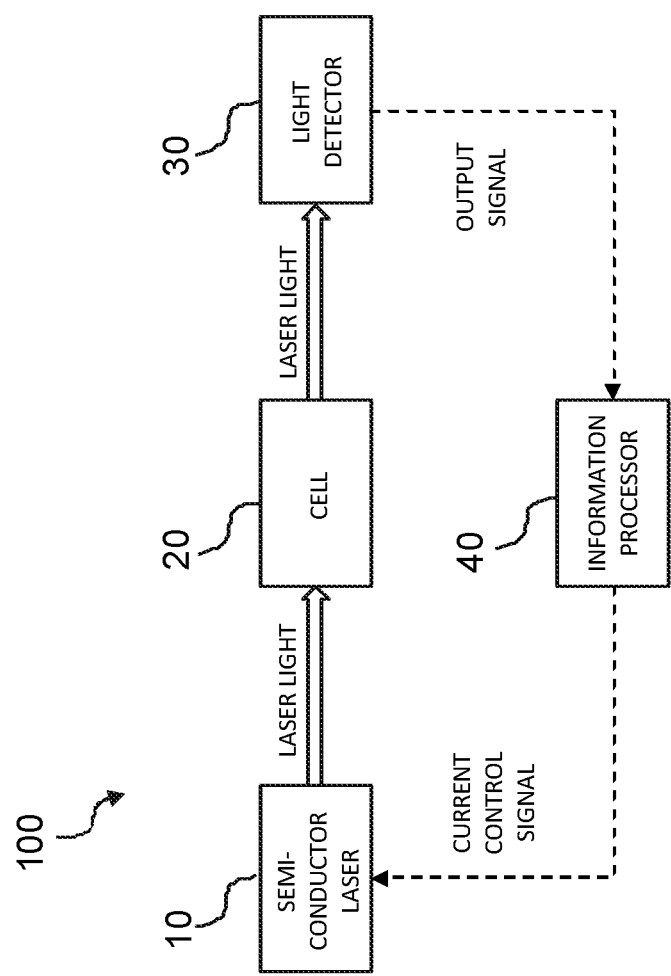
FIG. 1 is an overall schematic diagram of a gas analyzer according to one embodiment of the present invention.

A gas analyzer 100 of the present embodiment analyzes, for example, sample gas, such as exhaust gas exhausted from an internal combustion engine, by using an Infrared spectroscopy such as NDIR, and more specifically includes, as illustrated in FIG. 1: a semiconductor laser 10 serving as a light source; a multipass cell 20 into which the sample gas is introduced and also which causes multireflection of light from the semiconductor laser 10; a light detector 30 which detects the light emitted from the multipass cell 20; and an information processor 40 which analyzes a component contained in the sample gas based on a light intensity signal detected by the light detector 30.

The gas analyzer 100 according to the present invention has the multipass cell 20 which is discriminative, and each of sections other than the multipass cell 20 will be first described.

The semiconductor laser 10 is a quantum cascade laser (QCL) as one kind of the semiconductor laser 10 here, and oscillates mid-infrared (4 μm to 10 μm) laser light. This semiconductor laser 10 is capable of modulating (changing) an oscillation wavelength by a provided current (or voltage). Note that as long as the oscillation wavelength is variable, a laser of a different type may be used, and for example, a temperature may be changed to change the oscillation wavelength.

The light detector 30 uses a heat type such as a relatively low-cost Thermopile here, but a different type, for example, a quantum photoelectric device such as highly responsive HgCdTe, InGaAs, InAsSb, or PbSe may be used.

The information processor 40 includes: an analog electric circuit which includes a buffer, an amplifier, etc.; a digital electric circuit which includes a CPU, a memory, etc.; an AD converter and a DA converter which serve as a relay between the analog and digital electric circuits; and so on. As a result of cooperation of the CPU and surrounding devices thereof in accordance with a predetermined program stored in a predetermined region of the memory, the information processor 40 demonstrates functions of receiving an output signal from the light detector 30 and performing calculation processing on a value of the output signal to calculate concentration of a measurement target component.

Next, the multipass cell 20 as a characteristic of the gas analyzer 100 according to the present invention will be described in detail.

Figure 2:
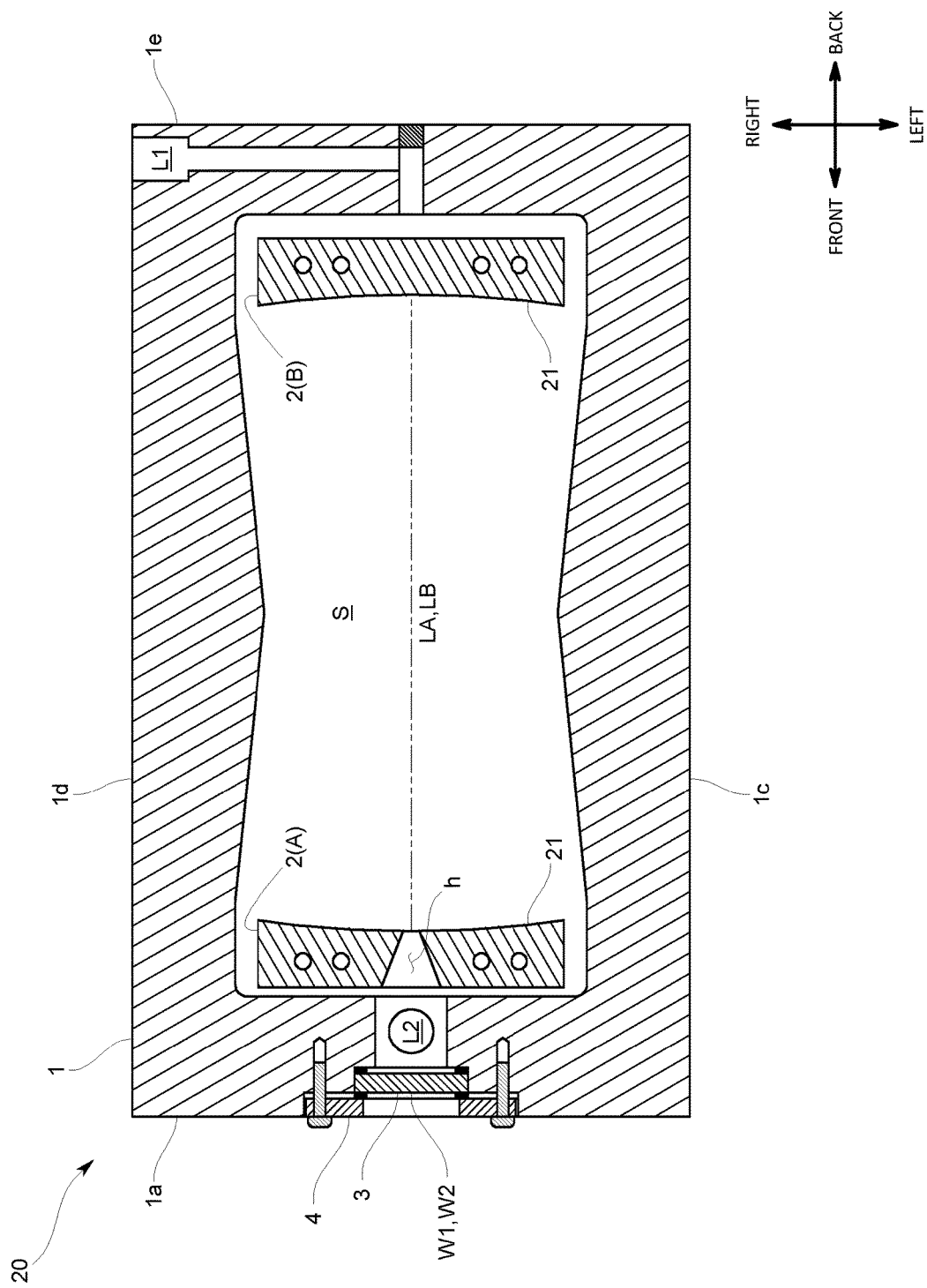
FIG. 2 is a cross-sectional view illustrating a configuration of a multipass cell of the same embodiment.

As illustrated in FIG. 2, the multipass cell 20 includes: a cell main body 1 with an inner space S into which sample gas is introduced; and a pair of mirrors 2 which are provided oppositely to each other in the cell main body 1. The multipass cell 20 is configured such that light incident from an incidence window W1 of the cell main body 1 is subjected to multireflection between the pair of mirrors 2 and emitted from an emission window W2 of the cell main body 1. Note that the incidence window W1 and the emission window W2 are formed of a transparent material such as quartz, calcium fluoride, or barium fluoride which is hardly subjected to light absorption in an absorption wavelength band of the measurement target component (for example, CO or CO2 here) contained in the sample gas.

The multipass cell 20 of the present embodiment is of a type called a Herriot cell, and uses spherical mirrors as the pair of mirrors 2. The mirrors 2 are arranged such that light axes LA and LB thereof overlap each other. The multipass cell 20 is designed such that light which has passed through a light passage hole h formed at one of the mirrors 2 is subjected to multireflection between reflecting surfaces 21 of the respective mirrors 2 so as to provide a predetermined number of paths and/or a predetermined light path length and the light passes through the light passage hole h again. Note that the light passage hole h here is formed so as to gradually widen from the reflecting surface 21 towards a rear surface thereof, but a shape of the light passage hole h may be changed as appropriate. Hereinafter, to make discrimination between the pair of mirrors 2, the mirror 2 formed with the light passage hole h is referred to as a first mirror 2A and the mirror 2 arranged oppositely to the first mirror 2A is referred to as a second mirror 2B. Note that arrangement and the number of light passage holes h may be changed as appropriate. For example, the light passage hole h may be formed not only at the first mirror 2A but also at the second mirror 2B or may be formed at only the second mirror 2B. Moreover, for example, as long as light is introduced into or out of a section between the mirrors 2A and 2B from surroundings of the first mirror 2A and the second mirror 2B, the light passage hole h may not be formed at both of the first mirror 2A and the second mirror 2B.

Figure 3:
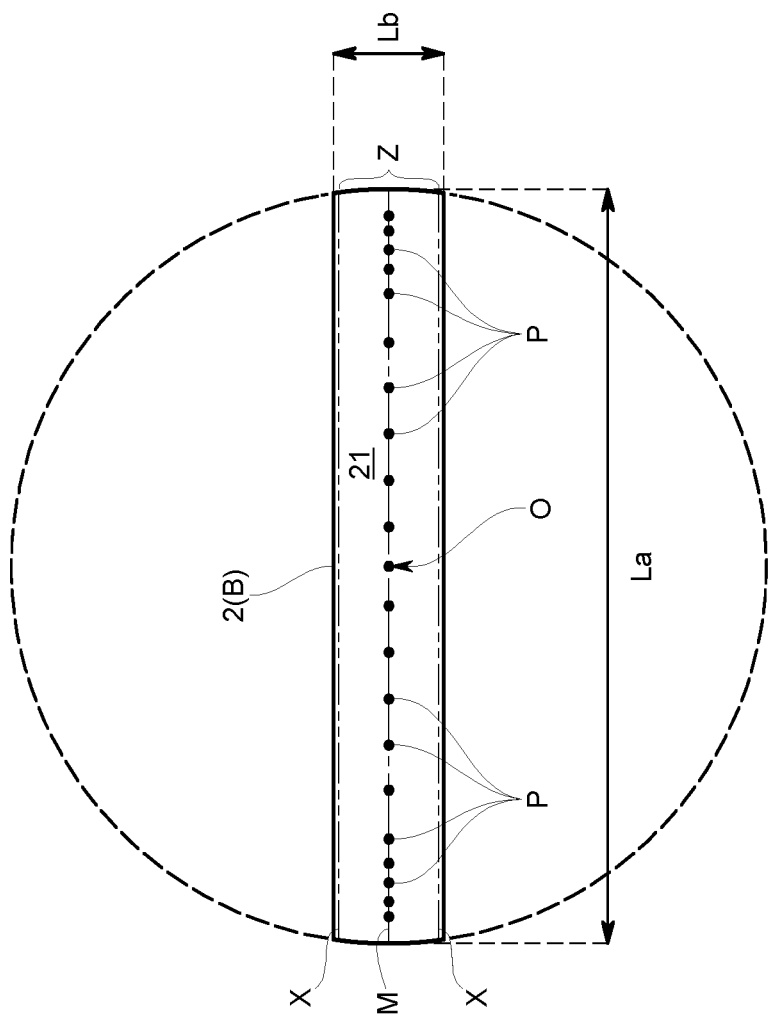
FIG. 3 is a plan view illustrating a configuration of each mirror of the same embodiment.

Thus, as illustrated in FIG. 3, the mirror 2 of the present embodiment is configured such that light spots P formed on the reflecting surface 21 of each mirror 2 are scattered in an elongated region Z of a predetermined width through light multireflection. Note that FIG. 3 illustrates the second mirror 2B representing the pair of mirrors 2, but the first mirror 2A also has the same configuration as that of the second mirror 2B excluding a point that the first mirror 2A is formed with the light passage hole h.

More specifically, as illustrated in FIG. 3, the elongated region Z is a region with, for example, a width of approximately several millimeters which is sandwiched between a pair of mutually parallel virtual lines X in a plan view of the reflecting surface 21 of the mirror 2, and the elongated region Z is a band-like region here. The virtual lines X regulate a region where the light spots P are to be scattered on the reflecting surface 21. The pair of virtual lines X in the present embodiment sandwich a center line M which passes through a center O of the mirror 2 and are also mutually parallel straight lines which are provided at equal distances from the center line M. The virtual lines X in FIG. 3 are illustrated on more inner sides than an outer edge of the mirror 2 for the sake of description, but the outer edge of the mirror 2 and the virtual lines X actually coincide, in other words, the entire reflecting surface 21 is set as the elongated region Z. However, the virtual lines X may be set on the even more inner sides than the outer edge of the mirror 2, in other words, the elongated region Z may be set on part of the reflecting surface 21. Note that the pair of virtual lines X do not necessarily have to be parallel to each other and are not limited to the straight lines but may be, for example, curved lines or wavy lines.

The pair of mirrors 2 are designed such that the light spots P are scattered on a line such as, for example, a straight line, a parabola, or an ellipse (including part of an ellipse) in the elongated region Z described above. More specifically, for the pair of mirrors 2, various parameters such as a mirror diameter, an inter-mirror distance, a diameter of the light passage hole h, and curvature radius of the reflecting surface 21 are appropriately set, and the mirror 2 is configured such that the light spots P are scattered on the center line M passing through the center O of the mirror 2.

Note that the light spots P do not necessarily have to be scattered on a single line and may be scattered on, for example, a plurality of straight lines, a plurality of parabolas, or a plurality of ellipses.

Next, listed as one example of a detailed method for manufacturing the mirrors 2 is a method for cutting prototype mirrors (for example, flat mirrors) as prototypes of the pair of mirrors 2 into elongated shapes and adjusting curvature of the reflecting surface of each prototype mirror such that the light spots P formed on the reflecting surfaces 21 of the pair of mirrors 2 are scattered in the elongated region Z described above through the light multireflection.

Each of the mirrors 2 as described above is of an elongated shape such that a longitudinal direction of the mirror 2 is parallel to a longitudinal direction of the elongated region Z. More specifically, a length La of the mirror 2 along the longitudinal direction of the elongated region Z is at least twice or more, more preferably, three times or more, and approximately six times in the present embodiment as long as a length Lb of the mirror 2 along a width direction orthogonal to the longitudinal direction of the elongated region Z.

Figure 4:
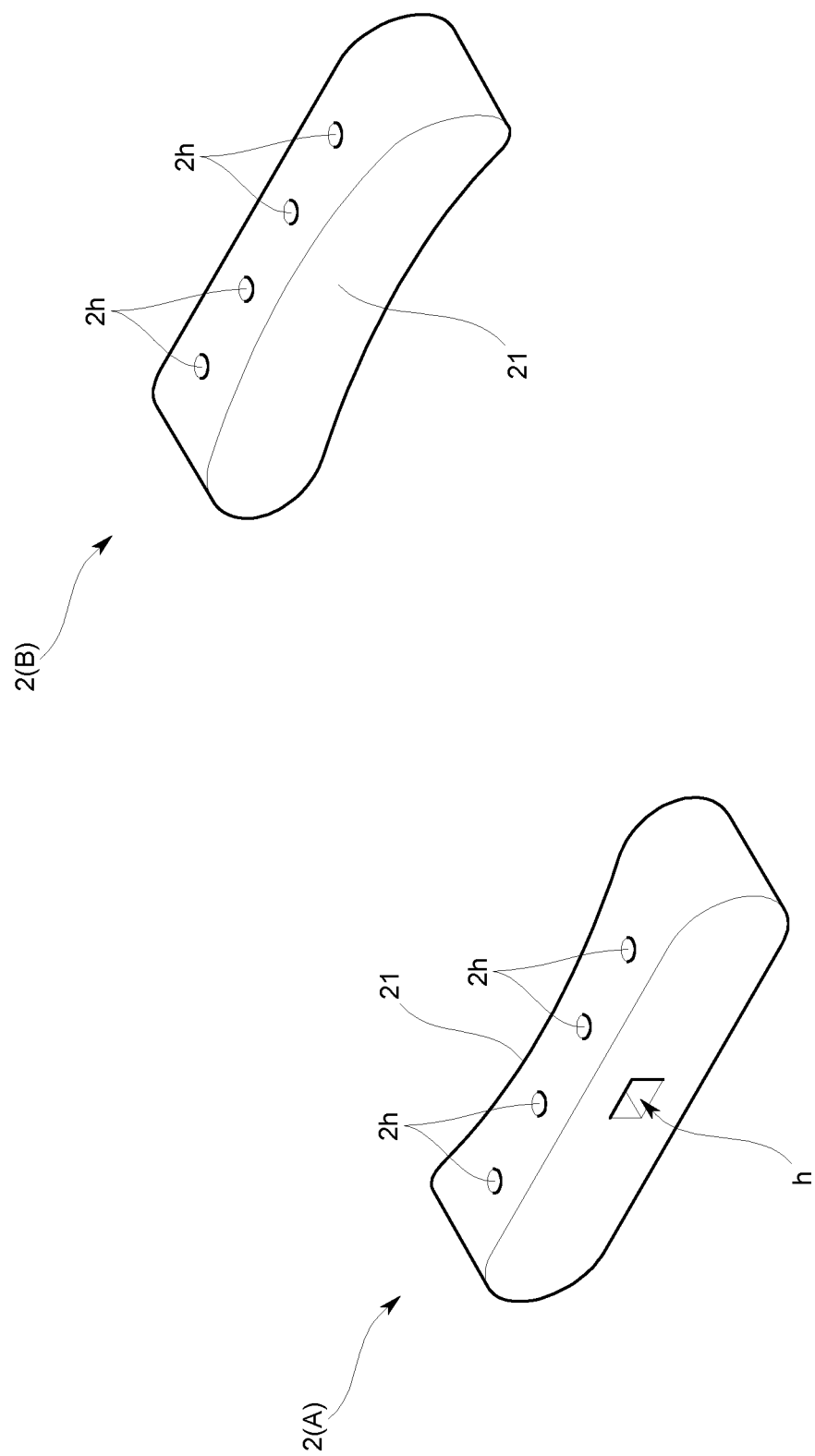
FIG. 4 is a perspective view illustrating a configuration of a pair of mirrors of the same embodiment.

As illustrated in FIG. 4, each mirror 2 is provided with a plurality of through holes 2h which are formed so as to penetrate through each mirror 2 in the aforementioned width direction. Each mirror 2 is screwed into the cell main body 1 with these through holes 2h in between. Note that the through holes 2h may be formed on rear surfaces of the reflecting surfaces 21.

Subsequently, the cell main body 1 will be described.

Figure 5:
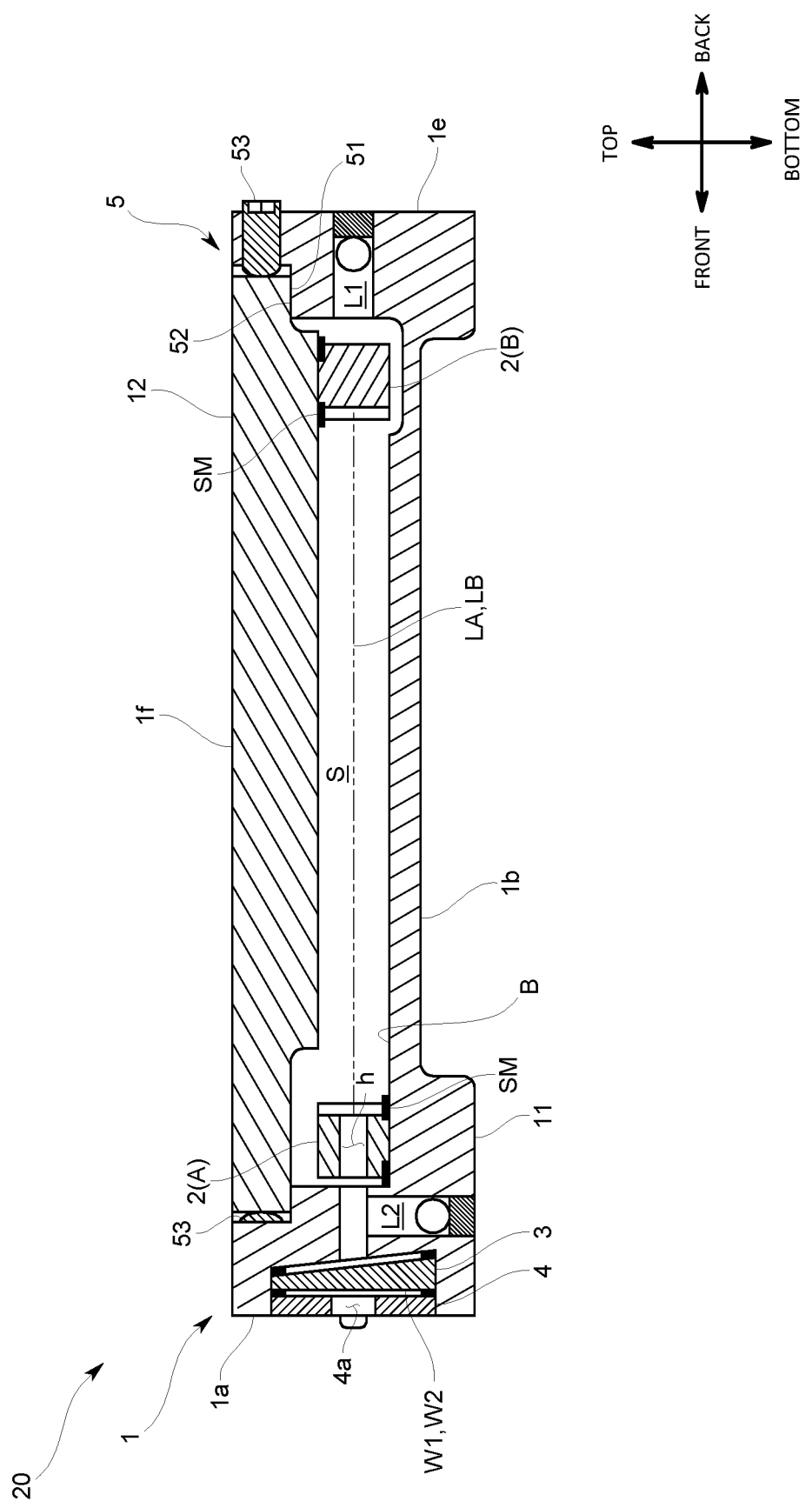
FIG. 5 is a cross-sectional view illustrating configuration of the multipass cell of the same embodiment.
Figure 6:
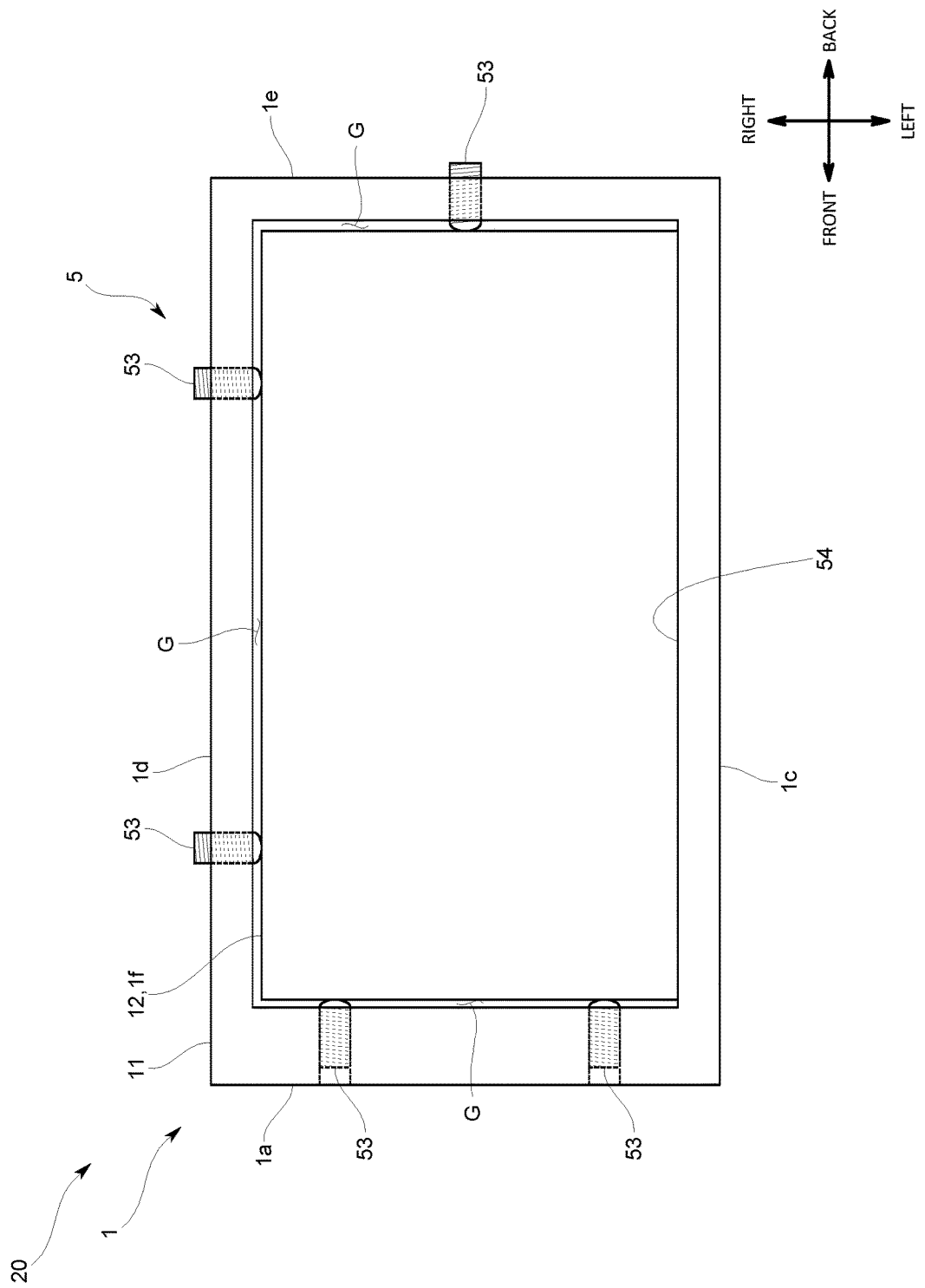
FIG. 6 is a plan view illustrating the configuration of the multipass cell of the same embodiment.

As illustrated in FIGS. 2, 5, and 6, the cell main body 1 is a housing of, for example, a substantially rectangular solid shape which stores the aforementioned pair of mirrors 2 in the inner space S, and the pair of mirrors 2 are arranged oppositely to each other along the longitudinal direction. In the present embodiment, each of the pair of mirrors 2 is of an elongated shape with a small thickness, and thus a flat shape with a small thickness is used as the cell main body 1. Consequently, an inner shape of the cell main body 1 is also flat, which can therefore provide the inner space S with small capacity, more specifically, a volume of the inner space S here is, for example, approximately several tens of milliliters. Note that the flat shape here may be changed to a rectangular solid shape or an elliptical shape in a plan view as appropriate.

Hereinafter, for the sake of description, a longitudinal direction of the cell main body 1 is referred to as a front-back direction, and a direction orthogonal to the longitudinal direction of the cell main body 1 is referred to as a horizontal direction, as illustrated in FIGS. 2 and 6, and a direction orthogonal to the front-back direction and the horizontal direction, that is, a thickness direction of the cell main body is referred to as a vertical direction, as illustrated in FIG. 5.

As illustrated in FIGS. 2 and 5, the cell main body 1 is formed with: an introduction path L1 which communicates with the inner space S and also which is provided for introducing sample gas from the outside; and a lead-out path L2 which communicates with the inner space S and also which is provided for leading out the sample gas to the outside.

One side wall (hereinafter referred to as a front wall 1a) of the cell main body 1 is provided with the aforementioned incidence window W1 and emission window W2 as illustrated in FIG. 5, and one light transmitting plate 3 provided at the front wall 1a is also used as both the incidence window W1 and the emission window W2 in the present embodiment. One light transmitting plate 3 can be used as both the incidence window W1 and the emission window W2 as described above, because the light passage hole h formed on one mirror 2 is used as the entrance and the exit of light. This configuration makes it possible to reduce the number of manufacturing parts and reduce the manufacturing cost.

Note that the incidence window W1 and the emission window W2 may be provided at mutually different side walls or may be formed by mutually different light transmitting plates 3.

The light transmitting plate 3 of the present embodiment is fitted in a recess formed at the front wall 1a with an elastic member such as a packing in between, and a pressing member 4 is further provided on a more outer side of the light transmitting plate 3 with an elastic member such as a packing in between. The pressing member 4 is of a flat plate-like shape which has, at a center part thereof, a light passage hole 4a through which light passes, and the pressing member 4 is screwed into the front wall 1a to thereby press and fix the light transmitting plate 3.

Note that to reduce noise (fringe noise) generated through light interference as a result of multireflection on an inside of the light transmitting plate 3, a surface of the light transmitting plate 3 on a side facing the inner space S is tilted with respect to a travel direction of the light from the semiconductor laser 10.

The cell main body 1 of the present embodiment is divided into two cell elements (hereafter referred to as a first cell element 11 and a second cell element 12) as illustrated in FIGS. 5 and 6. One (the first mirror 2A here) of the pair of mirrors 2 is fixed at the first cell element 11 while the other (the second mirror 2B here) of the pair of mirrors 2 is fixed at the second cell element 12.

More specifically, the first cell element 11 and the second cell element 12 are combined to thereby form the cell main body 1, in other words, the first cell element 11 and the second cell element 12 are one element and the other element obtained by dividing the cell main body 1 into two, forming, for example, a shape obtained by dividing a rectangular solid into two.

The first cell element 11 forms at least part of a bottom wall 1b of the cell main body 1, and the first mirror 2A is screwed into the bottom wall 1b with a seal member SM in between. The first cell element 11 of the present embodiment forms the bottom wall 1b and full circumference of side walls (that is, the front wall 1a, a left wall 1c, a right wall 1d, and a rear wall 1e) of the cell main body 1.

The second cell element 12 forms at least part of an upper wall 1f of the cell main body 1, and the second mirror 2B is screwed into a portion forming the upper wall 1f with a seal member SM in between. The second cell element 12 of the present embodiment forms almost the entire upper wall 1f of the cell main body 1.

As described above, since the first mirror 2A is fixed at the first cell element 11 and the second mirror 2B is fixed at the second cell element 12, combination of the first cell element 11 and the second cell element 12 positions in a vertical direction the first mirror 2A and the second mirror 2B. That is, the combination of the first cell element 11 and the second cell element 12 positions each of the mirrors 2A and 2B with respect to a reference plane B parallel to the light axes LA and LB of the mirrors 2A and 2B.

For example, in a case where a surface of the first cell element 11 on which the first mirror 2A is attached, that is, an inward surface of the bottom wall 1b is defined as the reference plane B, the first mirror 2A and the second mirror 2B are positioned in a direction orthogonal to the reference plane B. Note that the reference plane B may be a plane parallel to the light axes LA and LB, and thus may be an outward surface of the bottom wall 1b, may be a surface of the second cell element 12 on which the second mirror 2B is attached, that is, an inward surface of the upper wall 1f, or may be a surface on which the cell main body 1 is loaded.

Moreover, in a case where a first slide surface 51 and a second slide surface 52 to be described later on are parallel to each of the mirrors 2A and 2B, each of the first slide surface 51 and second slide surface 52 may be provided as the reference plane B.

In a state in which the first mirror 2A and second mirror 2B are positioned along the vertical direction, the light axes LA and LB of the respective first mirror 2A and second mirror 2B are at predetermined heights along the vertical direction from the reference plane B, more specifically, the light axes LA and LB are at the same heights from the reference plane B.

Thus, as illustrated in FIGS. 5 and 6, the cell main body 1 of the present embodiment includes a slide mechanism 5 which is provided between the first cell element 11 and the second cell element 12 and which slides one of the cell elements 11 and 12 with respect to the other of the cell elements 11 and 12.

The slide mechanism 5 causes slide movement of the first cell element 11 or the second cell element 12 along an in-plane direction parallel to the reference plane B, and the slide mechanism 5 causes slide movement of the second cell element 12 in the front-back direction and the horizontal direction in the present embodiment as illustrated in FIG. 6.

More specifically, the slide mechanism 5 has: the first slide surface 51 which is formed at the second cell element 12; and the second slide surface 52 with which this first slide surface 51 makes surface contact, and further has push-in members 53 which push in the second cell element 12 along a slide direction here.

In the present embodiment, the second cell element 12 is configured to make slide movement while making surface contact with the first cell element 11, the first slide surface 51 is a surface of the second cell element 12 opposing the first cell element 11, and the second slide surface 52 is a surface of the first cell element 11 opposing the second cell element 12. The first slide surface 51 and second slide surface 52 are both planes.

More specifically, a step part which is slightly larger than the upper wall 1*f* is formed on upper surfaces of the side walls of the cell main body 1, that is, the respective upper surfaces of the front wall 1*a*, the left wall 1*c*, the right wall 1*d*, and the rear wall 1*e*, and the upper wall 1*f* is loaded on the step parts. Consequently, as illustrated in FIG. 6, the upper wall 1*f* included in the second cell element 12 is arranged between the front wall 1*a*, the left wall 1*c*, the right wall 1*d*, and the rear wall 1*e* with a gap G in between, and the gap G permits the slide movement of the second cell element 12 in the front-back direction and the horizontal direction. Note that FIG. 6 illustrates a state in which the upper wall 1*f* included in the second cell element 12 is pushed in towards the left wall 1*c*, i.e., a state in which there is no gap G between the upper wall 1*f* and the left wall 1*c*.

The push-in members 53 are provided so as to move forward and backward with respect to the second cell element 12, more specifically, are bolts or the like which penetrate through the side walls and also which, for example, can be pushed and pulled by a driver.

In the present embodiment, the push-in members 53 are provided at a plurality of parts of the side walls. More specifically, the push-in members 53 are provided at at least one of the front wall 1*a* and the rear wall 1*e* and are also provided at at least one of the left wall 1*c* and the right wall 1*d*. The push-in members 53 here are provided at the three side walls, i.e., the front wall 1*a*, the rear wall 1*e*, and the right wall 1*d* but are not provided at the left wall 1*c*.

Moreover, the push-in members 53 are provided at the plurality of parts of at least one of the front wall 1*a*, the left wall 1*c*, the right wall 1*d*, and the rear wall 1*e*. The push-in members 53 here are provided at two parts of each of the front wall 1*a* and the right wall 1*d* while the push-in member 53 is provided at one part of the rear wall 1*e*. As described above, providing the plurality of push-in members 53 at the same side wall permits the slide mechanism 5 of the present embodiment to not only cause the slide movement of the second cell element 12 in the front-back direction and the horizontal direction but also slide the second cell element 12 while rotating the second cell element 12 around an axis along the vertical direction. Note that positions of the push-in members 53 and the number of push-in members 53 may be changed as appropriate.

Further, the slide mechanism 5 of the present embodiment has a guide surface 54 which makes contact with the second cell element 12 and also which regulates a slide direction of the second cell element 12. The guide surface 54 is a surface which extends along the slide direction of the second cell element 12, and here extends in the front-back direction to regulate the slide movement in the horizontal direction. More specifically, the guide surface 54 is a surface which regulates the push-in of the second cell element 12 by the push-in members 53 while making contact with the second cell element 12, and is a portion of the side wall (the left wall 1*c* here) of the cell main body 1 opposing the side wall of the second cell element 12. As described above, the guide surface 54 of the present embodiment is provided at the first cell element 11, but the guide surface 54 may be provided at a different member while the different member is put between the first cell element 11 and the second cell element 12.

With the multipass cell 20 configured as described above, the pair of mirrors 2 are configured such that the light spots P on the reflecting surface 21 are scattered in the elongated region Z of the predetermined width, and are formed into the elongated shapes along the longitudinal direction of the elongated region Z, thus permitting more drastic downsizing of the pair of mirrors 2 than that in a conventional case.

Consequently, a required volume of the inner space S of the cell main body 1 can be made very small, consequently making it possible to improve a replacement speed of the sample gas introduced into the inner space S, which permits a dramatic improvement in a response speed of analysis.

More specifically, the length La of the mirror 2 along the longitudinal direction of the elongated region Z is twice or more (approximately 6 times in the present embodiment) as long as the length Lb of the mirror 2 along the width direction orthogonal to the longitudinal direction of the elongated region Z. Then a length of the cell main body 1 along the longitudinal direction of the mirror 2 is longer than a length of the cell main body 1 along a width direction of the mirror 2, forming the cell main body 1 into a flat shape.

Consequently, downsizing of the mirrors 2 can be achieved while providing a long light path through multi-reflection, making it possible to make the volume of the inner space S much smaller than that of a conventional cell main body 1.

To achieve the downsizing of the mirrors 2 in the multi-pass cell 20, a possible mode is such that the reflecting surfaces 21 are provided as toroidal surfaces. However, to fabricate toroidal mirrors with high accuracy, an advanced processing technology is required, resulting in high manufacturing costs.

On the contrary, the multipass cell 20 of the present embodiment is a Heriot cell which uses the spherical mirrors as the pair of mirrors 2, thus permitting a reduction in the manufacturing costs while achieving the downsizing of the volume of the inner space S.

Moreover, since the toroidal mirror has two axes with mutually different curvature radiuses, for example, a position and orientation of each mirror needs to be severely determined upon assembly of the multipass cell in order to achieve light multireflection between the pair of mirrors.

On the contrary, the number of curvature radiuses of the spherical mirrors used as the pair of mirrors 2 is fixed as one in the present embodiment, thus providing more favorable assembly characteristics than that in a case where toroidal mirrors are used.

Further, the first mirror 2A is fixed at the first cell element 11, the second mirror 2B is fixed at the second cell element 12, and the slide mechanism 5 is provided between the first cell element 11 and the second cell element 12, thus permitting easy position adjustment of each mirror 2 only through sliding of the first cell element 11 or the second cell element 12 by the slide mechanism 5.

In addition, the pair of mirrors 2 are positioned with respect to the reference plane B in the direction orthogonal to this reference plane B and the slide mechanism 5 slides one of the cell elements with respect to the other of the cell elements in the in-plane direction parallel to the reference plane B, and thus can make the position adjustment of the mirrors 2 in the direction orthogonal to the reference plane B unnecessary. That is, the sliding of the first cell element 11 or the second cell element 12 along the in-plane direction parallel to the reference plane B makes it possible to complete the position adjustment of each mirror 2, resulting in more simplified positioning of the mirrors 2.

Furthermore, the slide mechanism 5 has the second slide surface 52 which is formed at the first cell element 11 and the first slide surface 51 which is formed at the second cell element 12, thus permitting formation of the slide mechanism 5 with a small number of components without placing a different member between the two cell elements.

Moreover, since the slide mechanism 5 has the guide surface 54 which makes contact with the second cell element 12 and also which regulates the slide direction of the second cell element 12, the siding of the second cell element 12 in the slide direction regulated by the guide surface 54 makes it possible to complete the position adjustment of the pair of mirrors 2, permitting simplification of the positioning of the pair of mirrors 2.

Moreover, the first cell element 11 and the second cell element 12 are obtained by dividing the cell main body 1 of a substantially rectangular solid shape into two, thus permitting formation of the multipass cell 20 with a minimum possible number of components.

Further, since the second cell element 12 forms part of the upper wall 1f of the cell main body 1, removal of the second cell element 12 from the first cell element 11 permits, for example, simple cleaning of an inside of the cell main body 1, which can improve maintainability of the cell main body 1. In particular, upon analysis of exhaust gas as in the present embodiment, contamination of the inside of the cell main body 1 can easily be cleaned. Moreover, the combination of the first cell element 11 and the second cell element 12 permits alignment of the light axes of the pair of mirrors 2 after maintenance such as cleaning, which can therefore improve the maintainability and the assembly characteristics at once.

Note that the present invention is not limited to the embodiments described above.

For example, the second cell element 12 forms the upper wall 1f of the cell main body 1 in the embodiment above, but as long as the first cell element 11 forms at least part of the cell main body 1 and the first mirror 2A is fixed, and as long as the second cell element 12 forms at least part of the cell main body 1 and the second mirror 2B is fixed, shapes of the first cell element 11 and the second cell element 12 can be changed to various kinds.

Figure 7:
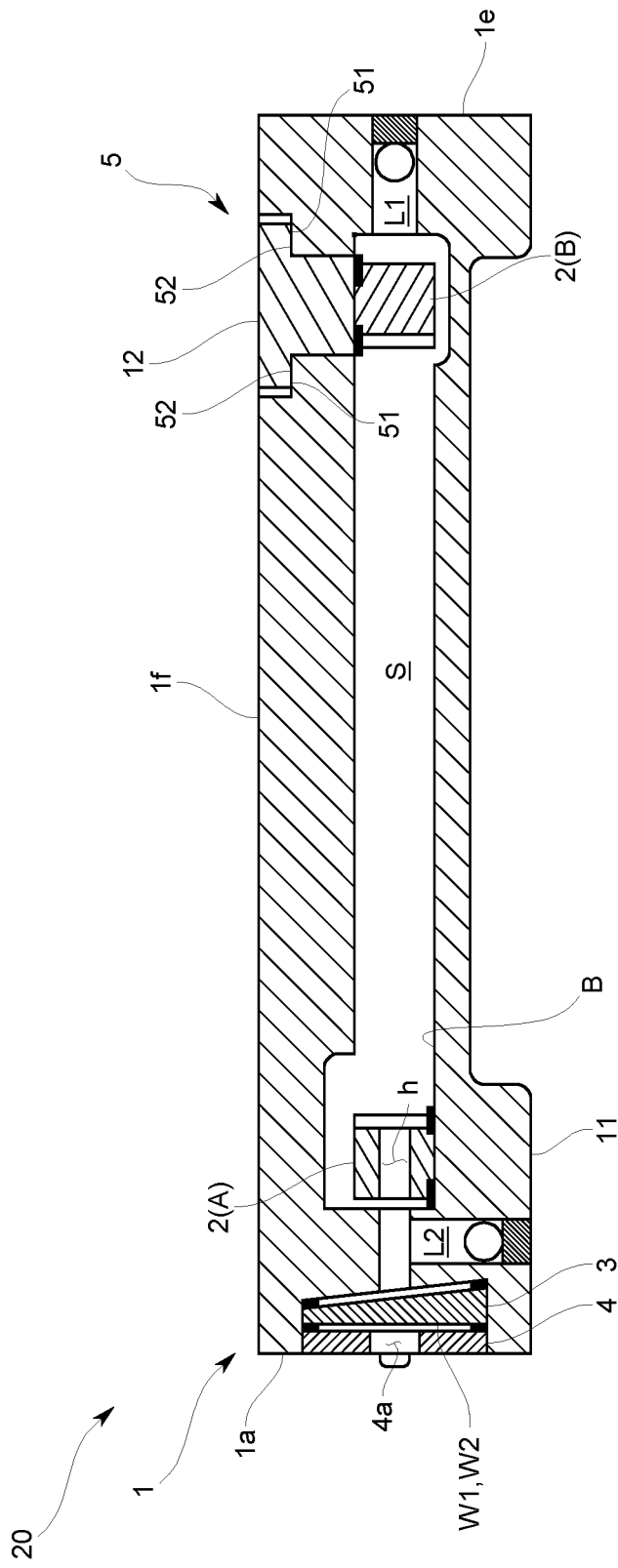
FIG. 7 is a cross-sectional view illustrating a configuration of a multipass cell of a modified embodiment.
Figure 8:
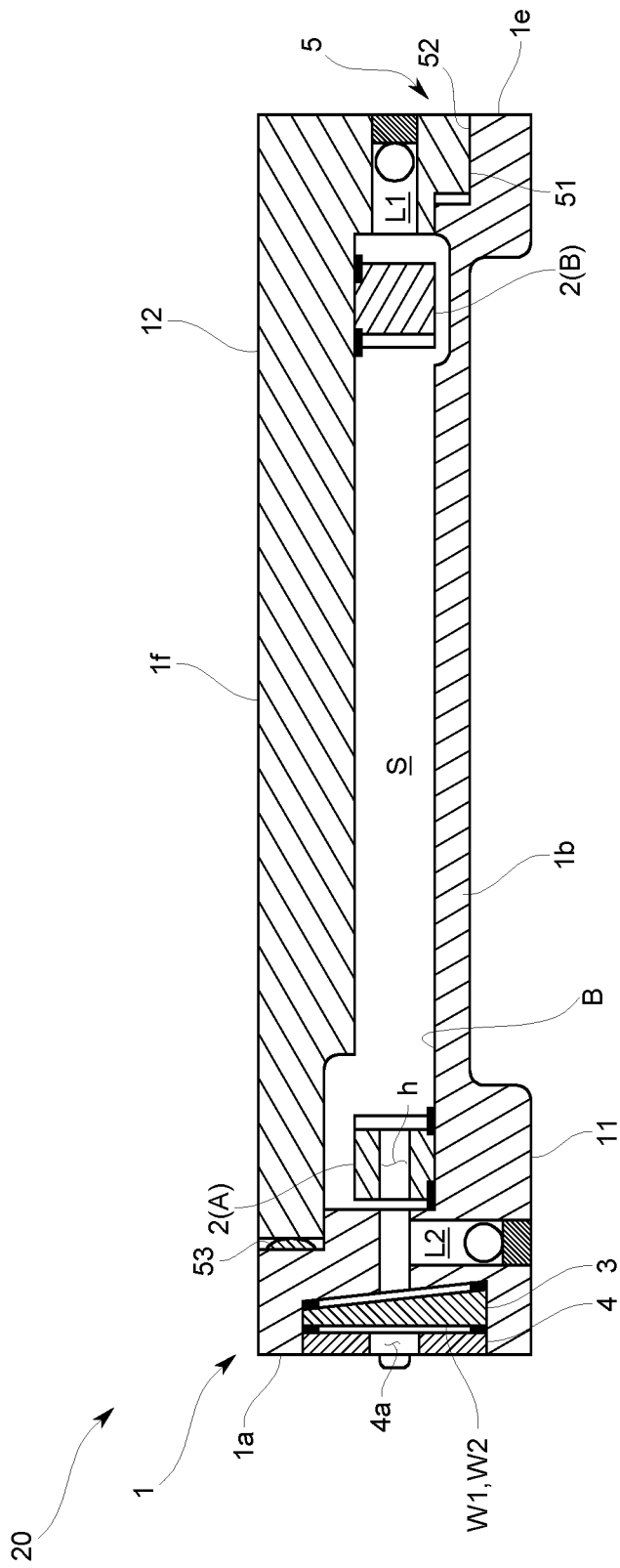
FIG. 8 is a cross-sectional view illustrating the configuration of the multipass cell of the modified embodiment.

More specifically, the second cell element 12 may form part the upper wall 1f of the cell main body 1 as illustrated in FIG. 7, or the first cell element 11 may form at least the bottom wall 1b and the rear wall 1e and the second cell element 12 may form at least the upper wall 1f and the front wall 1a as illustrated in FIG. 8.

Moreover, the slide mechanism 5 of the embodiment above causes the slide movement of the second cell element in the front-back direction and the horizontal direction, but the slide mechanism 5 may cause the slide movement in only one of the front-back direction and the horizontal direction or may cause the slide movement in the vertical direction (the thickness direction of the cell main body 1). Further, the slide mechanism 5 may cause slide movement of the first cell element with respect to the second cell element.

The cell main body 1 may be divided into three or more cell elements or may be formed of a single cell element, and the shape of the cell main body 1 is not limited to that in the embodiment above. Further, the cell main body 1 may not include the slide mechanism 5.

The method for manufacturing the pair of mirrors 2 is not limited to that in the embodiment above, and for example, a pair of prototype mirrors as the pair of mirrors 2 are first manufactured. This prototype mirror is a spherical mirror with a reflecting surface of a circular shape in a plan view.

For each prototype mirror, various parameters such as a mirror diameter, an inter-mirror distance, a diameter of a light passage hole, and a curvature radius of a reflecting surface are appropriately set so that light spots formed on the reflecting surface of each prototype mirror are scattered in the elongated region described above through light multireflection between the mirrors.

Then cutting and removing a portion of each prototype mirror other than the elongated region results in manufacture of the pair of mirrors into elongated shapes along the elongated region. Note that as long as the elongated region Z is left, the whole of each prototype mirror other than the elongated region does not necessarily have to be removed.

Figure 9:
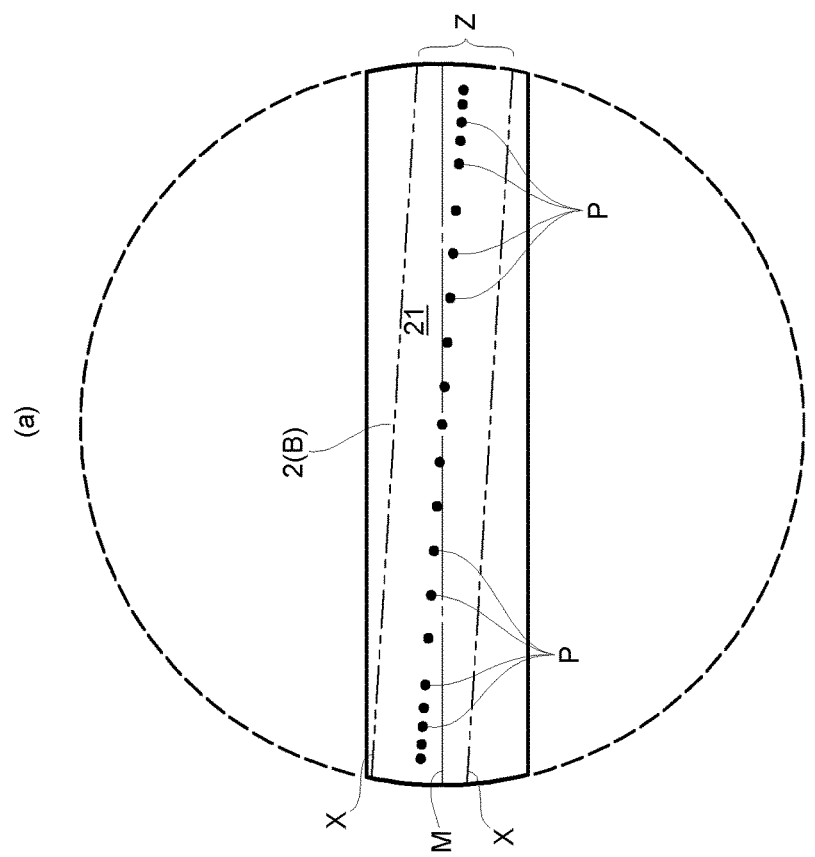
FIGS. 9($a$) and 9($b$) are diagrams illustrating light spots formed on a reflecting surface of a mirror of the modified embodiment.
Figure 9:
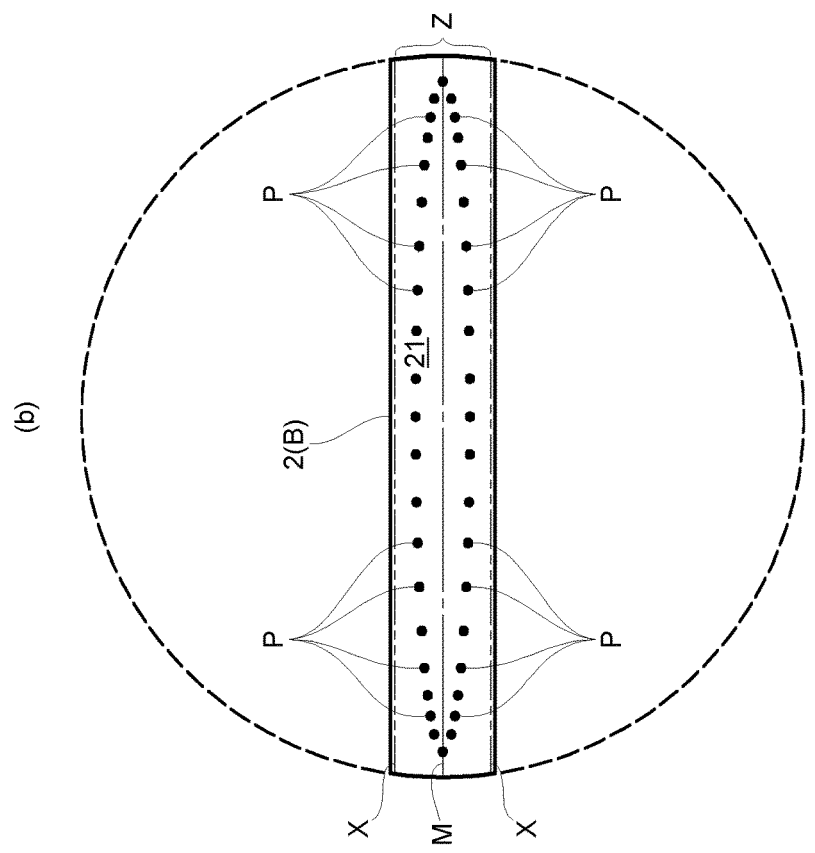

Moreover, the embodiment has been described above, referring to the case where the longitudinal direction of the mirror 2 and the longitudinal direction of the elongated region Z are parallel to each other, but, for example, the longitudinal direction of the elongated region Z may be tilted with respect to the longitudinal direction of the mirror 2 as illustrated in FIG. 9A.

Further, the light spots P do not have to be scattered on a straight line, and, for example, may be scattered on an ellipse as illustrated in FIG. 9B.

The slide mechanism 5 is configured in the embodiment above such that the first cell element 11 and the second cell element 12 make surface contact with each other, but the slide mechanism 5 may be configured such that a different member is provided between the first cell element 11 and the second cell element 12 and sliding is achieved through surface contact of the different member with the first cell element 11 and the second cell element 12. Note that the number of different members is not limited to one and a plurality of different members may be provided.

Moreover, the sample gas (sample) may be not only exhaust gas but also the air or a liquid or a solid as a sample. In this sense, the present invention is applicable not only to gas as a measurement target component but also to a liquid or a solid. Moreover, the measurement target can be used not only for absorbance of the light transmitted through but also for calculation of absorbance caused by the reflection.

The embodiment has been described above, referring to the case where the multipass cell 20 is a Heriot cell, but the multipass cell 20 may be a white cell.

The pair of mirrors 2 are spherical mirrors in the embodiment above, but toroidal mirrors may be used as the pair of mirrors 2.

The embodiment has been described above, referring to the case where the light source is a quantum cascade laser (QCL) as one type of a semiconductor laser, but the light source may be a semiconductor laser other than the quantum cascade laser. Moreover, the light source does not necessarily have to be a semiconductor laser and may be, for example, a lamp using a filament or may be an LED light source. Further, the light source is not limited to the one which emits mid-infrared light but may be the one which emits near infrared light or far infrared light or may be the one which emits ultraviolet light.

The embodiment has been described above on the assumption that the gas analyzer 100 adopts the NDIR method, but the gas analyzer according to the present invention may adopt, for example, an FTIR method or an NDUV method.

Further, the following description may be provided for analysis principles.

First, before describing the analysis principles, the functions of the information processor 40 will be described.

Figure 10:
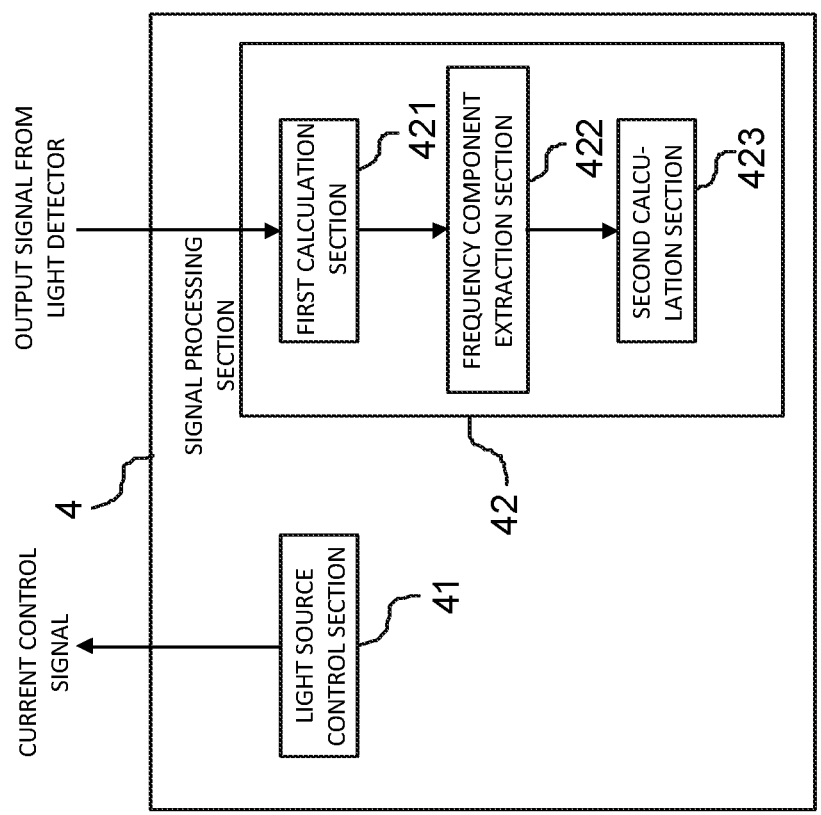
FIG. 10 is a functional block diagram of an information processor according to the modified embodiment.

As illustrated in FIG. 10, the information processor 40 exerts the functions as a light source control section 41 which controls output of the light source 10 and a signal processing section 42 which receives the output signal from the light detector 30 and performs the calculation processing on the value of the output signal to calculate concentration of the measurement target component.

The light source control section 41 outputs a current (or voltage) control signal to thereby control a current source (or a voltage source) of the semiconductor laser 10, thereby changing a drive current (or a drive voltage) thereof with a predetermined frequency and in turn modulating the oscillation wavelength of laser light outputted from the semiconductor laser 10 with the predetermined frequency.

Figure 11:
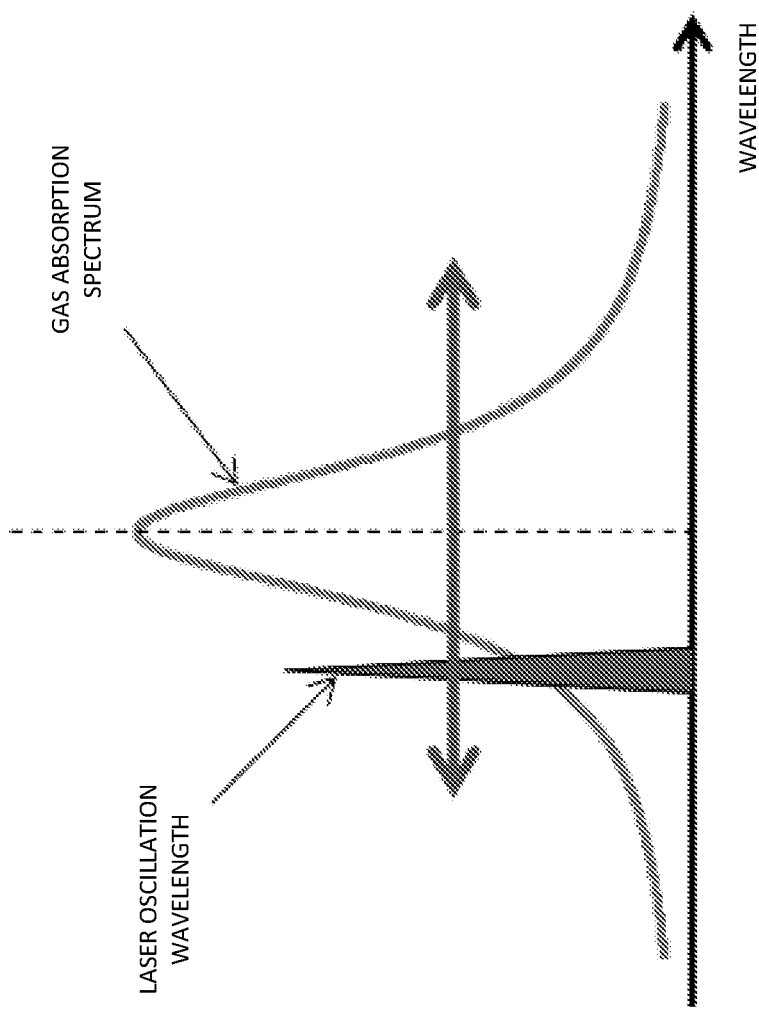
FIG. 11 is a schematic diagram illustrating a method for modulating a laser oscillation wavelength according to the modified embodiment.
Figure 12:
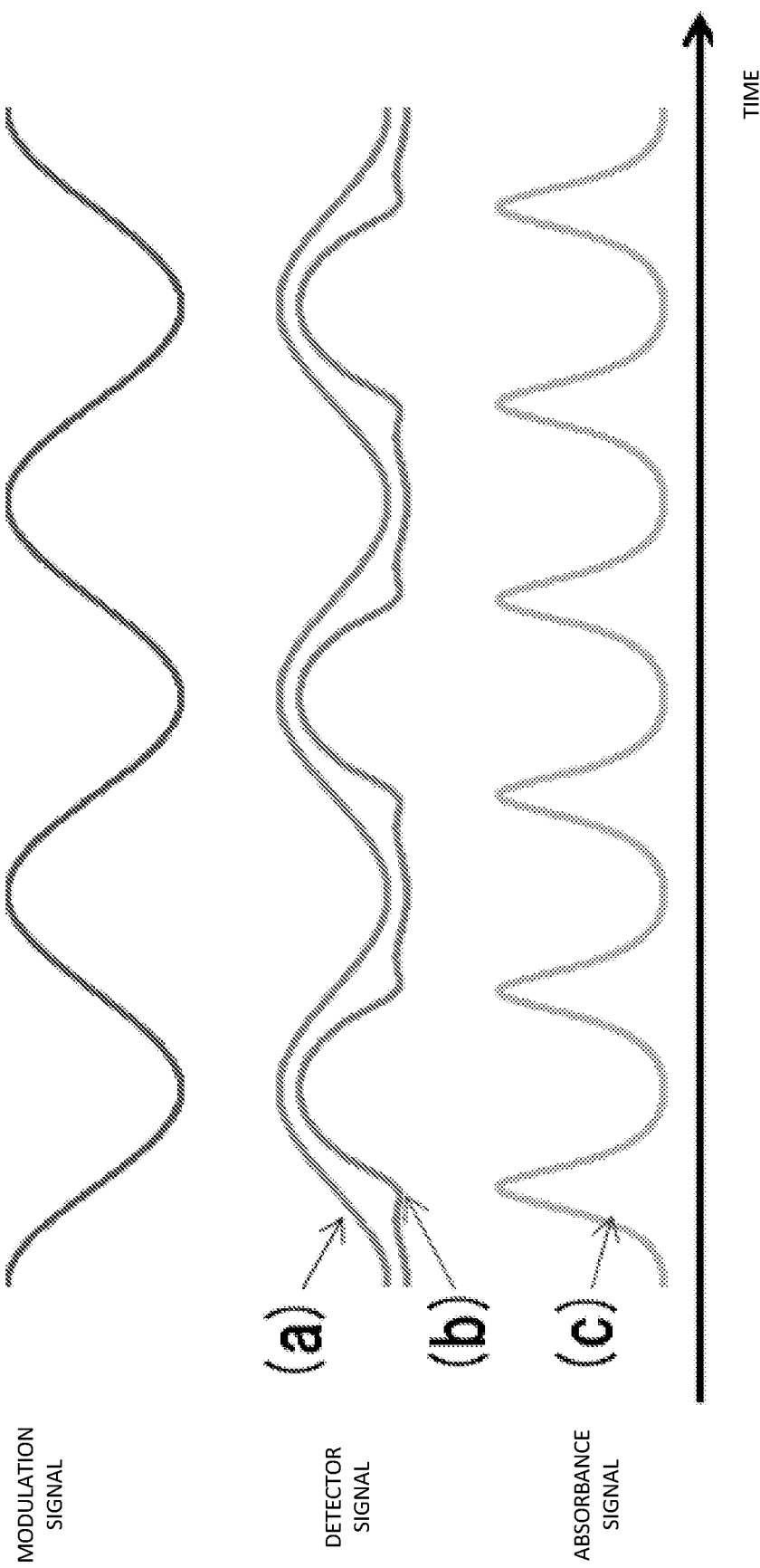
FIG. 12 is a diagram illustrating one example of a modulation signal, an output signal of a light detector, and measurement results according to the modified embodiment.

In the present embodiment, the light source control section 41 changes the drive current to a sinusoidal form and modulates the oscillation frequency to a sinusoidal form (see a modulation signal of FIG. 12). Moreover, as illustrated in FIG. 11, the oscillation wavelength of the laser light described above is adapted to be modulated where a peak of a light absorption spectrum of the measurement target component is defined as the center.

The signal processing section 42 includes: a first calculation section 421, a frequency component extraction section 422, a second calculation section 423, etc.

The first calculation section 421 calculates a logarithm (hereinafter referred to as an intensity ratio logarithm) of a ratio between a light intensity of laser light (hereinafter referred to as measurement target light) which is transmitted through the multipass cell 20 while the sample gas is sealed and light absorption is caused by the measurement target component therein and a light intensity of laser light (hereinafter referred to as reference light) which is transmitted through the multipass cell 20 in a state in which light absorption is substantially zero.

More specifically, the former and latter light intensities are each measured by the light detector 30 and measurement result data obtained through the measurement is stored into a predetermined region of the memory, and the first calculation section 421 calculates the aforementioned intensity ratio logarithm with reference to the measurement result data.

Thus, the former measurement (hereinafter referred to as sample measurement) is performed, needless to say, for each sample gas. The latter measurement (hereinafter referred to as reference measurement) may be performed either before or after the sample measurement, or may be performed, for example, only once at appropriate timing and results of the measurement may be stored into the memory and used commonly with the sample measurement.

Note that in the present embodiment, to provide the state in which the light absorption is substantially zero, zero gas, for example, $N_2$ gas with which light absorption becomes substantially zero in a wavelength band where light absorption of the measurement target component is observed is sealed in the multipass cell 20, but different gas may be used or an inside of the multipass cell 20 may be vacuumed.

The frequency component extraction section 422 performs lock-in detection of the intensity ratio logarithm (hereinafter referred to as absorbance signal), which has been calculated by the first calculation section 421, with a reference signal having a frequency n-times (where n is an integer of 1 or more) as large as the modulation frequency described above and extracts a frequency component included in the reference signal from the aforementioned intensity ratio logarithm. Note that the lock-in detection may be performed through digital calculation or calculation made by an analog circuit. Moreover, the extraction of the frequency component may be performed through not only the lock-in detection but also through a method such as, for example, Fourier series expansion.

The second calculation section 423 calculate the concentration of the measurement target component based on results of the detection performed by the frequency component extraction section 422.

Next, one example of operation of this gas analyzer 100 will be described in combination with detailed description of the various sections described above.

First, as described above, the light source control section 41 controls the semiconductor laser 10 and modulates a wavelength of the laser light with the aforementioned modulation frequency where the peak of the absorption spectrum of the measurement target component is defined as the center.

Next, when the zero gas has been sealed into the multipass cell 20 automatically or by an operator, the first calculation section 421 which has detected this phenomenon performs the reference measurement.

More specifically, the output signal from the light detector 30 is received while the zero gas is sealed in the multipass cell 20 and a value of the output signal is stored into a measurement result data storage section. The value of the output signal of the light detector 30 in the reference measurement, that is, an intensity of the reference light is expressed in a time series graph as illustrated in FIG. 12A. That is, only a change in light output by modulation of the drive current (voltage) of the laser is expressed in the output signal of the light detector 30.

Thus, when the sample gas has been sealed into the multipass cell 20 automatically or by the operator, the first calculation section 421 performs the sample measurement. More specifically, the output signal from the light detector 30 is received while the sample gas is sealed in the multipass cell 20, and the value of the output signal is stored into a predetermined region of the memory. The value of the output signal of the light detector 30 in the sample measurement, that is, the intensity of the measurement target light is expressed in a time series graph as illustrated in FIG. 12B. It is found that a peak caused by absorption appears for each half cycle of modulation.

Next, the first calculation section 421 synchronizes each measurement data with a modulation cycle and calculates an intensity ratio logarithm of the light intensity of the measurement target light and the light intensity of the reference light. More specifically, calculation equal to an expression (Expression 1) below is performed:

$$A(t) = -\ln\left(\frac{D_m(t)}{D_z(t)}\right) \quad \text{[Expression 1]}$$

where $D_m(t)$ denotes the intensity of the measurement target light;
$D_z(t)$ denotes the intensity of the reference light; and
$A(t)$ denotes the intensity ratio logarithm (absorbance signal).

The absorbance signal is expressed in a graph with time plotted at a horizontal axis as illustrated in FIG. 12C.

Note that as a way of obtaining the intensity ratio logarithm, the ratio between the intensity of the measurement target light and the intensity of the reference light may first be calculated and then the logarithm thereof may be obtained, or a logarithm of the measurement target light and a logarithm of the intensity of the reference light may each be obtained and they may be subtracted.

Next, the frequency component extraction section 422 performs lock-in detection of the aforementioned intensity ratio logarithm with a reference signal having a frequency twice as large as the modulation frequency, that is, extracts the frequency component twice as large as the modulation frequency, and stores data thereof (hereinafter referred to as lock-in data) into a predetermined region of the memory. Note that the lock-in data may be obtained by subtracting what is obtained by subjecting each of the logarithm of the measurement target light and the logarithm of the intensity of the reference light to the lock-in detection.

A value of the lock-in data becomes a value proportional to the concentration of the measurement target component, and based on the value of the lock-in data, the second calculation section 423 calculates a concentration indication value indicating the concentration of the measurement target component.

Thus, with such configuration, even upon fluctuation in laser light intensity due to some factor, given offset is only added to the aforementioned intensity ratio logarithm, causing no change in the waveform. Therefore, a value of each frequency component calculated by performing lock-in detection of the intensity ratio logarithm does not change and the concentration indication value does not change, which can therefore expect highly accurate measurement.

A reason for this will be described as follow.

Fourier series expansion of the absorbance signal $A(t)$ is typically expressed by an expression (Expression 2) below.

Note that $a_n$ in (Expression 2) denotes a value proportional to the concentration of the measurement target component, and the second calculation section 423 calculates the concentration indication value indicating the concentration of the measurement target component based on the value $a_n$.

$$A(t) = a_0 + \sum_{n=1}^{\infty} a_n \cos(2\pi n f_m t + \phi_n) \quad \text{[Expression 2]}$$

where $f_m$ denotes a modulation frequency; and
n denotes a multiple with respect to the modulation frequency.

On the other hand, $A(t)$ is also expressed in the expression (Expression 1) described above.

Next, the absorbance signal $A'(t)$ in a case where the laser light intensity fluctuates by $\alpha$ times due to some reason during the measurement is expressed as in an expression (Expression 3) below.

$$A'(t) = -\ln\left(\frac{\alpha D_m(t)}{D_z(t)}\right) = -\ln\left(\frac{D_m(t)}{D_z(t)}\right) - \ln(\alpha) = A(t) - \ln(\alpha) \quad \text{[Expression 3]}$$

As is clear from the expression (Expression 3), the absorbance signal $A'(t)$ is obtained by only adding $-\ln(\alpha)$ as a fixed value to the absorbance signal $A(t)$ when the laser light intensity does not fluctuate, thus proving that the value $a_n$ of each frequency component does not change even upon a change in the laser light intensity.

Therefore, there is no influence on the concentration indication value determined based on the value of the frequency component twice as large as the modulation frequency.

The above is the example of operation of the gas analyzer 100 in a case where an interference component other than the measurement target component is not included in the sample gas.

Next, an example of operation of the gas analyzer 100 in a case where one or a plurality of interference components (for example, $H_2O$) having light absorption in a peak light absorption wavelength of the measurement target component are included in the sample gas will be described.

First, principles will be described.

Shapes of light absorption spectra of the measurement target component and the interference component are different, and thus waveforms of the absorbance signals in a case where these components are independently present are different and ratios of the respective frequency components are different (linear independence). Using this, relationship between the value of each frequency component of the measured absorbance signal and each frequency component of the absorbance signals of the previously obtained measurement target component and interference component is used to solve simultaneous expressions, whereby concentration of the measurement target component for which an influence of interference has been corrected can be provided.

Where $A_m(t)$ and $A_i(t)$ respectively denote absorbance signals per unit concentration in a case where the measurement target component and the interference component are each independently present and $a_{nm}$ and $a_{ni}$ denote the frequency components of the respective absorbance signals, expressions (Expressions 4 and 5) below are formed.

$$A_m(t) = a_{0m} + \sum_{n=1}^{\infty} a_{nm} \cos(2\pi n f_m t + \phi_n) \quad \text{[Expression 4]}$$

-continued $$A_i(t) = a_{0i} + \sum_{n=1}^{\infty} a_{ni}\cos(2\pi n f_m t + \phi_n)$$ [Expression 5]

The absorbance signal value A(t) in a case where concentration of the measurement target component and the interference component are present as $C_m$ and $C_i$ is expressed by an expression (Expression 6) below by linearity of each absorbance.

[Expression 6]
$$A(t) = C_m A_m(t) + C_i A_i(t)$$
$$= C_m\left(a_{0m} + \sum_{n=1}^{\infty} a_{nm}\cos(2\pi n f_m t + \phi_n)\right) +$$
$$C_i\left(a_{0i} + \sum_{n=1}^{\infty} a_{ni}\cos(2\pi n f_m t + \phi_n)\right)$$
$$= a_{0m}C_m + a_{0i}C_i + \sum_{n=1}^{\infty}(a_{nm}C_m + a_{ni}C_i)\cos(2\pi n f_m t + \phi_n)$$

Where $a_1$ and $a_2$ respectively denote frequency components of $f_m$ and $2f_m$ in A(t), simultaneous expressions (Expression 7) below are formed based on the expression (Expression 6) described above.

$$a_{1m}C_m + a_{1i}C_i = a_1$$
$$a_{2m}C_m + a_{2i}C_i = a_2$$ [Expression 7]

Each of frequency components $a_{nm}$ and $a_{ni}$ (where n is a natural number, and n=1,2 here) in a case where the measurement target component and the interference component are each independently present can previously be obtained through flow of each span gas, and thus concentration $C_m$ of the measurement target gas from which the influence of interference is removed can be determined through simple and reliable calculation of solving the simultaneous expressions (Expression 7) described above.

The gas analyzer 100 operates based on the aforementioned principles.

Specifically, the gas analyzer 100 in this case stores the frequency components $a_{1m}$, $a_{2m}$, $a_{1i}$, and $a_{2i}$ of the respective absorbance signals in a case where the measurement target component and the interference component are each independently present by, for example, previous measurement through the previous flow of span gas into a predetermined region of the memory. More specifically, as is the case with the aforementioned example, the intensity of the measurement target light and the intensity of the reference light are measured for each of the measurement target component and the interference component to calculate intensity ratio logarithms (absorbance signals) thereof, and for example, lock-in detection is performed based on the aforementioned intensity ratio logarithms to obtain the frequency components $a_{1m}$, $a_{2m}$, $a_{1i}$, and $a_{2i}$, and the frequency components are then stored. Note that instead of the frequency components, the absorbance signals $A_m(t)$ and $A_i(t)$ per unit concentration may be stored and the frequency components $a_{1m}$, $a_{2m}$, $a_{1i}$, and $a_{2i}$ may be calculated based on the expression (Expression 4) described above.

Then the gas analyzer 100 specifies the measurement target component and the interference component by, for example, inputting by an operator.

Next, the first calculation section 421 calculates the intensity ratio logarithm A(t) in accordance with the expression (Expression 1) described above.

Then the frequency component extraction section 422 performs lock-in detection of the intensity ratio logarithm with the reference signal having the modulation frequency $f_m$ and the frequency $2f_m$ twice as large as the modulation frequency $f_m$ to extract the frequency components $a_1$ and $a_2$ (lock-in data) and store the frequency components $a_1$ and $a_2$ into the predetermined region of the memory.

Then the second calculation section 423 assigns the expression (Expression 7) described above with the values $a_1$ and $a_2$ of the lock-in data and the values of the frequency components $a_{1m}$, $a_{2m}$, $a_{1i}$, and $a_{2i}$ stored in the memory or calculation equal thereto is performed to calculate concentration (or concentration indication value) $C_m$ indicating the concentration of the measurement target gas from which the influence of interference has been removed. At this point, the concentration (or the concentration indication value) $C_i$ of each interference component may be calculated.

Note that even in a case where two or more interference components are present, higher-order frequency components the number of which is equal to the number of interference components can be added and simultaneous expressions whose number of elements is equal to the number of component types can be solved to thereby determine concentration of the measurement target component from which the influence of interference has been removed in the same manner.

Specifically, in a case where n-types of gas are present through combination of the measurement target component and the interference component, where the frequency component of the kth-gas type $i \times f_m$ is $a_{ik}$ and concentration of the k-th gas type is $C_k$, expressions (Expression 8) below are formed:

$$a_{11}C_1 + a_{12}C_2 + a_{13}C_3 + \ldots + a_{1n}C_n = a_1$$ [Expression 8]
$$a_{21}C_1 + a_{22}C_2 + a_{23}C_3 + \ldots + a_{2n}C_n = a_2$$
$$a_{31}C_1 + a_{32}C_2 + a_{33}C_3 + \ldots + a_{3n}C_n = a_3$$
$$\vdots$$
$$a_{n1}C_1 + a_{n2}C_2 + a_{n3}C_3 + \ldots + a_{nn}C_n = a_n$$

Solving n-element simultaneous expressions expressed by the expressions (Expression 8) can determine the concentration of each gas of the measurement target component and the interference component.

Moreover, a harmonic component of which order is higher than n may be added to create simultaneous expressions whose number of elements is larger than the number of gas types and determine concentration of each gas by a least-square method, thereby making it possible to achieve concentration determination with a smaller error for measurement noise.

Figure 13:
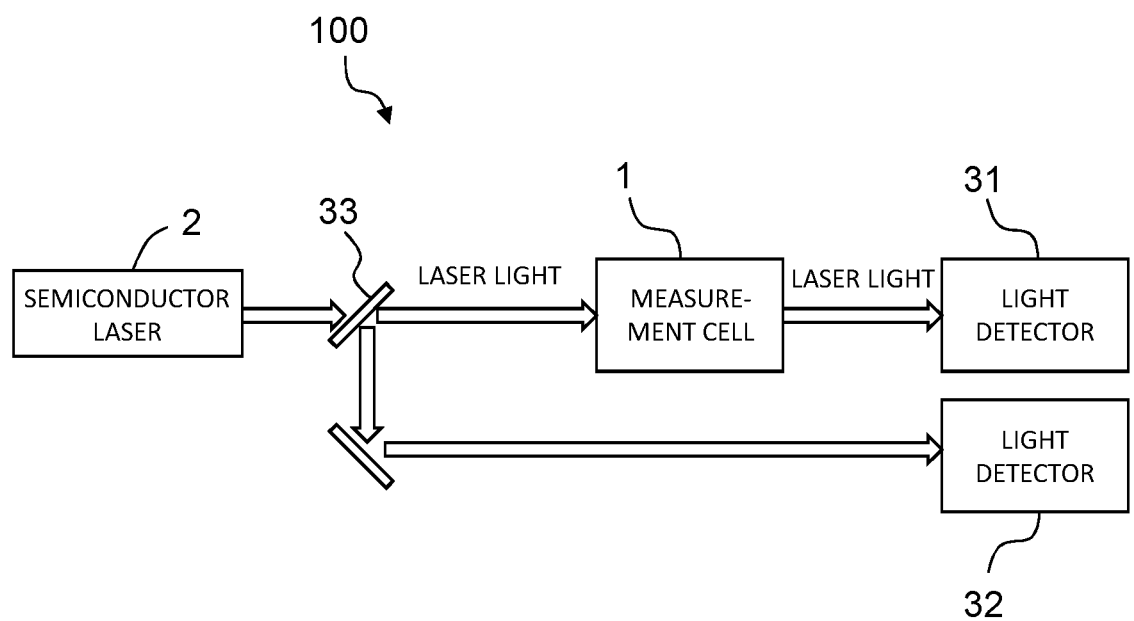
FIG. 13 is a schematic diagram illustrating main parts of an analyzer of the modified embodiment.

The sample measurement and the reference measurement are performed by the single light detector in the embodiment described above, but as illustrated in FIG. 13, two light detectors 31 and 32 may be used with the light detector 31 provided for the sample measurement and the light detector 32 provided for the reference measurement. In this case, light from the light source 2 is branched by a half mirror 33. Moreover, a reference cell may be arranged on a light path for the reference measurement. Note that it is possible that zero gas or reference gas whose concentration is already known is sealed into the reference cell.

The present invention is not limited to the embodiment above, and it is needless to say that various modifications can be made within a range not departing from spirits of the present invention.

REFERENCE SIGNS LIST

100 Gas analyzer
20 Multipass cell
1 Cell main body
2A,B Mirror
Reflecting surface
P Light spot
Z Elongated region
11 First cell element
12 Second cell element
5 Slide mechanism
51 First slide surface
52 Second slide surface
53 Push-in member
54 Guide surface

The invention claimed is:

1. A multipass cell comprising a cell main body with an inner space into which sample gas is introduced and a pair of mirrors including a first mirror and a second mirror provided oppositely to each other in the inner space, wherein light incident from an incidence window of the cell main body is subjected to multireflection between the pair of mirrors and is emitted from an emission window of the cell main body, wherein:
the pair of mirrors is configured such that light spots formed on a reflecting surface of each of the mirrors are scattered in an elongated region of a predetermined width through the light multireflection; and
each of the mirrors is formed into an elongated shape along a longitudinal direction of the elongated region.

2. The multipass cell according to claim 1, wherein:
a length of each of the mirrors along the longitudinal direction of the elongated region is twice or more as long as a length of each of the mirrors along a width direction orthogonal to the longitudinal direction of the elongated region.

3. The multipass cell according to claim 2, wherein
the length of each of the mirrors along the longitudinal direction is three times or more as long as the length of each of the mirrors along the width direction.

4. The multipass cell according to claim 1, wherein
each of the mirrors is configured such that the light spots are scattered in the elongated region by use of a spherical mirror.

5. The multipass cell according to claim 1, wherein
the light spots are scattered on a straight line, a parabola, or an ellipse in the elongated region.

6. The multipass cell according to claim 1, wherein
a length of the cell main body along a longitudinal direction of the mirror is longer than a length of the cell main body along a width direction of the mirror.

7. The multipass cell according to claim 1, wherein:
the cell main body has at least two cell elements forming the cell main body;
the first mirror is fixed at one of the at least two cell elements and the second mirror is fixed at another one of the at least two cell elements; and
a slide mechanism of sliding, with respect to the one of the cell elements, the another one of the cell elements is provided between the at least two cell elements.

8. The multipass cell according to claim 7, wherein:
each of the mirrors is positioned in a direction orthogonal to a predetermined reference plane with respect to the predetermined reference plane; and
the slide mechanism slides, with respect to the one of the cell elements, the another one of the cell elements along an in-plane direction parallel to the reference plane.

9. The multipass cell according to claim 7, wherein
the slide mechanism has: a first slide surface formed at the one of the cell elements; and a second slide surface formed at the another one of the cell elements and making surface contact with the first slide surface.

10. The multipass cell according to claim 7, wherein
the slide mechanism has a guide surface making contact with the another one of the cell elements and regulating a slide direction of the another one of the cell elements.

11. A gas analyzer comprising:
the multipass cell according to claim 1;
a light source emitting light to the incidence window;
a light detector detecting the light emitted from the emission window; and
an information processor analyzing the sample gas based on a light intensity signal detected by the light detector.

12. A method for manufacturing a mirror for a multipass cell as a pair of mirrors including a first mirror and a second mirror being provided oppositely to each other in an inner space of a cell main body into which sample gas is introduced and forming the multipass cell with the cell main body, wherein
a pair of prototype mirrors including a first prototype mirror and a second prototype mirror serving as prototypes of the pair of mirrors are cut into elongated shapes, and the shapes of the pair of prototype mirrors are changed such that light spots formed on a reflecting surface of the pair of mirrors are scattered in an elongated region of a predetermined width through light multireflection.

* * * * *